(12) United States Patent
Verger et al.

(10) Patent No.: US 8,148,096 B2
(45) Date of Patent: Apr. 3, 2012

(54) MICROTITRATION PLATES COMPRISING WELLS COATED WITH A LIPID SUBSTRATE AND A METHOD OF PREPARING

(75) Inventors: Robert Verger, Marseilles (FR); Carole Serveau-Avesque, Marseilles (FR); Henri Chahinian, Marseilles (FR)

(73) Assignee: Centre National de la Recherche Scientifique, Paris (FR)

( * ) Notice: Subject to any disclaimer, the term of this patent is extended or adjusted under 35 U.S.C. 154(b) by 383 days.

(21) Appl. No.: 11/884,139

(22) PCT Filed: Feb. 10, 2006

(86) PCT No.: PCT/FR2006/000310
§ 371 (c)(1),
(2), (4) Date: Mar. 31, 2008

(87) PCT Pub. No.: WO2006/085009
PCT Pub. Date: Aug. 17, 2006

(65) Prior Publication Data
US 2008/0193958 A1      Aug. 14, 2008

(30) Foreign Application Priority Data
Feb. 11, 2005 (FR) ................................. 05 01425

(51) Int. Cl.
*C12Q 1/34* (2006.01)
(52) U.S. Cl. ......................................... 435/18; 435/198
(58) Field of Classification Search ................ 435/18, 435/198
See application file for complete search history.

(56) References Cited

U.S. PATENT DOCUMENTS

2004/0014133 A1* 1/2004 Price-Jones et al. ........... 435/7.1
2009/0246811 A1* 10/2009 Arakawa et al. ................ 435/19
2009/0246812 A1* 10/2009 Nakamura et al. .............. 435/19

FOREIGN PATENT DOCUMENTS

EP        0 245 799 A        11/1987

OTHER PUBLICATIONS

Pencreac'h G. et al. An Ultraviolet Spectrophotometric Assay for Measuring Lipase Activity Using Long Chain Triacyglycerols from *Aleurites fordii* Seeds. Analytical Biochemistry 303(1)17-24, 2002.*
Pencrea'h G. et al. An Ultraviolet Spetrophotometric Assay for Measuring Lipase Activity . . . Analytical Biochemistry 303 17-24, 2002.*
Pencreac'h et al., "An Ultraviolet Spectrophotometric Assay for Measuring Lipase Activity using Long-Chain Triacyglycerols from *Aleurites fordii* Seeds," Anal. Biochem., vol. 303, No. 1, pp. 17-24 (2002).
Beisson et al., "Methods for Lipase Detection and Assay: A Critical Review," Eur. J. Lipid. Sci. Tech., vol. 102, No. 2, pp. 133-153 (Feb. 2000).

* cited by examiner

*Primary Examiner* — Ralph Gitomer
(74) *Attorney, Agent, or Firm* — Young & Thompson

(57) ABSTRACT

A method for the detection and/or measurement in vitro of a lipase or phospholipase activity, including the addition of a sample likely to contain said lipase or phospholipase into the wells of microtitration plates coated with a layer of a lipid substrate which is able to be hydrolyzed by the lipase or phospholipase by releasing α-eleostearic acid, and the detection and/or the measurement of the lipase or phospholipase activity by UV spectrophotometry of the α-eleostearic acid released during the previous stage. The application of this method to the in vitro diagnosis of pathologies linked to an increase in the plasma lipase level.

2 Claims, 4 Drawing Sheets

Figure 4A
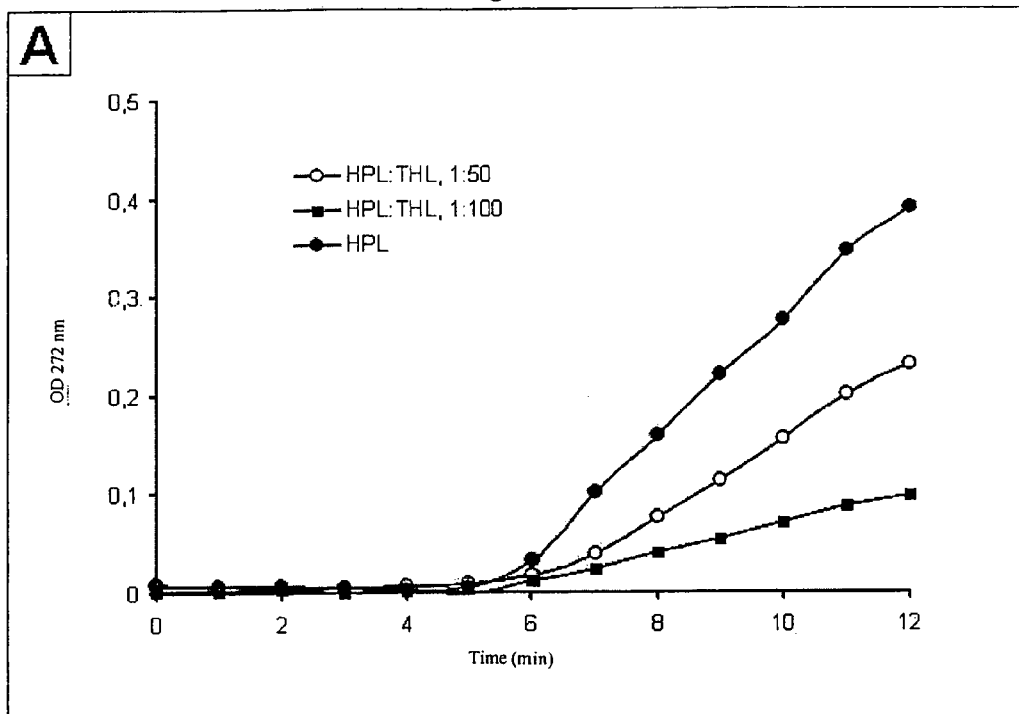
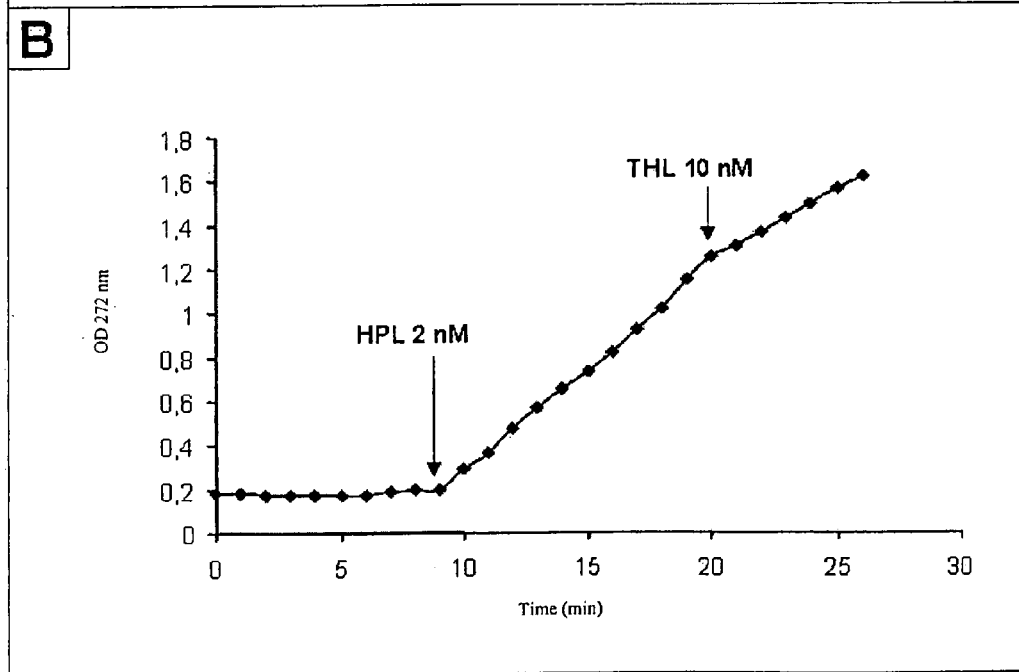
Figure 4B

MICROTITRATION PLATES COMPRISING WELLS COATED WITH A LIPID SUBSTRATE AND A METHOD OF PREPARING

A subject of the present invention is a method for the high-speed detection and/or measurement in vitro of a lipase or phospholipase activity, as well as its applications.

The development of analytical methods for the detection and assay of lipases is the subject of work over many years (Beisson F., Tiss A., Riviere C. and Verger R. (2000) Methods for lipase detection and assay: a critical review. Eur. J. Lipid Sci. Technol. 2: 133-153).

Naturally fluorescent triglycerides for detecting very low lipase activities have been used with the aim of characterizing the kinetic and enantioselective properties of the lipases generated by the "phage display" technique (Beisson F., Ferte N., Nari J., Noat G., Arondel V. and Verger R. (1999). Use of naturally fluorescent triacylglycerols from Parinari glaberrimum to detect low lipase activities from *Arabidopsis thaliana* seedlings. J. Lipid Res. 40: 2313-2321).

The principle of this method resides on the one hand in the presence in the parinarium oil of a naturally fluorescent fatty acid (parinaric acid) which has four conjugated double bonds and as a result absorbs light in the ultraviolet region and reemits it via a fluorescence phenomena. Under the hydrolytic action of the lipases, the parinaric acid is released from the original triglyceride in order to be solubilized in a micellar phase. This phase change (from an emulsified phase to a micellar phase) is accompanied by a variation of fluorescence spectral emission which has been exploited to monitor, with great sensitivity, the development over time of the hydrolysis reaction.

One of the limitations of this fluorescent method is linked to the oxidizability by atmospheric oxygen of the four conjugated double bonds of parinaric acid. This is why the Inventors have transposed the same measurement principle to an oil extracted from Chinese wood (Tung oil) and used since antiquity in the manufacture of Chinese lacquers. This oil contains a very high proportion of α-eleostearic acid which only has three conjugated double bonds and is not fluorescent but absorbs ultraviolet light. This acid is also very much less oxidizable than parinaric acid. Therefore the Inventors have used on the one hand the ultraviolet absorption properties of alpha-eleostearic acid and on the other hand, the phase change described previously (from an emulsified phase to a micellar phase) for developing a so-called in "emulsion" method described in the article by Pencreac'h G., Graille J., Pina M. and Verger R. (2002). An ultraviolet spectrophotometric assay for measuring lipase activity using long-chain triacylglycerols from *Aleurites fordii* seeds. Anal. Biochem. 303: 17-24.

Within the framework of the development of these works, the Inventors have used the purified triglycerides of tung oil to coat the wells of microtitration plates (constituted by plastic material which is non-absorbent in the ultraviolet) with a very thin film (equivalent to a few hundreds of monomolecular layers). The Inventors have demonstrated that this thin film of triglycerides remains perfectly adsorbed on the well walls, even after rinsing with different aqueous buffers. Under the hydrolytic action (at the oil-water interface) of different lipases, as described previously, α-eleostearic acid is released and solubilized in the micellar phase. As a result, its ultraviolet absorption spectrum is modified and on the other hand, the optical path is considerably increased as a result of passing from the adsorbed state to the soluble state, which constitutes a significant advantage for the "coating" technique.

The present invention results from the demonstration by the Inventors of the fact that this novel technique of "coating" lipids (natural triglycerides or synthetic esters) has the following advantages compared to the previous "emulsion" technique:
 better storage over time of the adsorbed (or "coated") lipid substrates in the wells of the microtitration plates,
 a higher activity of the lipases on the "coated" substrate than on the emulsion substrate,
 better reproducibility of the experiments with the "coated" substrate,
 a more favourable signal-to-noise ratio due to the increase in the optical path as a result of passing from the adsorbed state to the soluble state.

Thus, the purpose of the present invention is to provide a novel method for measurement of the lipase activity which is more specific, quantitative and sensitive than the methods described up to now in this field, and which makes it possible to measure very low lipolytic activities (equivalent to a minimal quantity of approximately 2 ng for the *Thermomyces lanuginosus* Lipase, "TLL"), by using a natural substrate of lipases.

The purpose of the present invention is also to provide a novel method for measurement of the lipase activity making it possible to screen at high flow rates the numerous lipase mutants likely to be generated thanks to the "phage display" technique.

The purpose of the present invention is also to provide a novel method for measurement of the lipase activity at high flow rates in order to select enantioselective mutants and lipases, using chiral esters, which are of pharmaceutical and biotechnological interest, containing alpha-eleostearic acid. These thus-selected mutants could serve as enzymatic catalysts for the asymmetrical synthesis of molecules of pharmaceutical and agri-food interest.

The purpose of the present invention is also to provide a novel method for measurement of the lipase activity which can be used in human clinical medicine, for the measurement of plasmatic lipasemia, during the early diagnosis of various pancreatic diseases.

The invention relates to a method for the detection and/or measurement in vitro of a lipase or phospholipase activity which is characteristic of a lipase or phospholipase of natural or synthetic origin in a sample likely to contain this lipase or phospholipase, characterized in that it comprises:
 the addition of the above-mentioned sample likely to contain said lipase or phospholipase in aqueous solution, into the wells of microtitration plates coated with a layer of approximately 0.5 to approximately 5 μm, and preferably approximately 1 μm in thickness of a lipid substrate which is able to be hydrolyzed by said lipase or phospholipase by releasing α-eleostearic acid which solubilizes in the micellar phase in said aqueous solution,
 the detection and/or the measurement of the lipase or phospholipase activity by spectrophotometry in the UV absorption spectrum of the α-eleostearic acid released during the previous stage.

By lipase or phospholipase of natural or synthetic origin is meant any lipase or phospholipase of mammals or microorganisms (bacteria, fungi etc.), if appropriate modified by the mutation of one or more amino acids. The lipase activity can be measured in a standard fashion according to the methods described in particular in Beisson et al. (Beisson F., Tiss A., Riviere C. and Verger R. (2000) Methods for lipase detection and assay: a critical review. Eur. J. Lipid Sci. Technol. 2: 133-153). The lipase or phospholipase activity can for example be measured by the method described in Wolf et al. (Wolf C., Sagaert L. and Bereziat G. (1981) A sensitive assay of phospholipases using the fluorescent probe 2-parinaroyl-lecithin. Biochem. Biophys. Res. Com. 99: 275-283) where a synthetic phospholipid containing parinaric acid was used for measuring the enzymatic activity of snake venom phospholipase A2.

More particularly, the invention relates to a method as defined above, characterized in that the lipid substrate which is able to be hydrolyzed by said lipase or phospholipase by releasing the α-eleostearic acid, is a lipid chosen from molecules of industrial and/or pharmaceutical interest onto which the α-eleostearate groups are bound covalently, and in particular is chosen from:

the purified triglycerides of tung oil of general formula

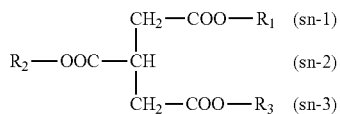

where $R_1$, $R_2$, $R_3$ represent residues of identical or different fatty acids, comprising approximately 12 to 20 carbon atoms, and preferably comprising 18 carbon atoms, and optionally having one or more unsaturations, (sn signifying stereospecific numbering)

the di- and monoglycerides, or the cholesterol esters or phospholipids containing 1 or 2 chains of α-eleostearate in a suitable position according to the type of regioselectivity of the sought lipases or phospholipases, the citronellol α-eleostearate of the following formula:

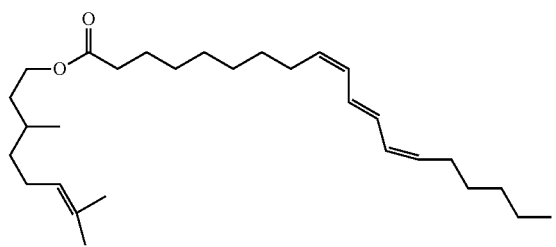

or the acid esters of α-eleostearate with other alcohols or molecules which are prochiral or chiral and are of pharmaceutical interest such as propanolol, sotalol or carvedilol used as β-blockers, or with molecules of industrial interest such as menthol (terpene derivative of aromatic interest).

In particular, the synthetic triglycerides where $R_1$ and $R_3$ as defined above represent identical or different fatty acid residues, comprising approximately 12 to 20 carbon atoms, and preferably 18 carbon atoms, and optionally having one or more unsaturations, and where $R_2$ represents α-eleostearic acid making it possible to screen specific sn-2 lipases (i.e. capable of releasing the fatty acid present in the sn-2 position of the triglycerides). In a comparable fashion, the synthetic phospholipids containing α-eleostearic acid in the sn-1 and/or sn-2 position make it possible to measure the enzymatic activities of the phospholipases A1 and/or phospholipases A2, a phospholipase A1 being defined as an enzyme capable of releasing the fatty acid present in the sn-1 position of the glycerophospholipids and a phospholipase A2 being defined as an enzyme capable of releasing the fatty acid present in the sn-2 position of the glycerophospholipids.

In tung oil, the fatty acids in significant quantity are: α-eleostearic acid (70-80%), oleic acid (10%) and linoleic acid (15%), as described in particular in Radunz et al. (A. Radunz, P. He and G. H. Schmid, Analysis of the seed lipids of *Aleurites montana*. Z. Naturforsch. 53 (1998), pp. 305-310).

The invention also relates to a method as defined above, characterized in that it comprises, prior to the addition of the sample likely to contain the lipase or phospholipase into the wells of microtitration plates, a stage of adding to the wells of microtitration plates coated in lipid substrate, a buffer solution constituted by Tris and bile salts (NaTDC) and, if appropriate β-cyclodextrin, in particular in the following proportions: NaTDC (4 mM) and β-cyclodextrin (3 mg/mL).

A subject of the invention is also a method as defined above, characterized in that the microtitration plates coated with the lipid substrate are as obtained by:

the addition of a composition comprising the lipid substrate in solution in an appropriate solvent capable of being evaporated off under vacuum, such as hexane or petroleum ether, this addition being if appropriate carried out after washing the wells of said plates with said solvent, evaporation under vacuum of said solvent until the formation of a coating of said lipid substrate of approximately 0.5 to approximately 5 μm, and preferably approximately 1 μm in thickness on the walls of the wells of the microtitration plates.

A more particular subject of the invention is a method as defined above, of in vitro measurement of plasmatic lipasemia in humans or animals, characterized in that the sample containing the lipase is a blood sample taken from a human or an animal.

Therefore, the invention also relates to the application of a method as defined above, to the in vitro diagnosis of pathologies linked to an increase in the plasma lipase level in humans or animals, compared to the plasma lipase level in a healthy individual.

The invention relates more particularly to the above-mentioned application of a method as defined above, with in vitro diagnosis:

of pancreatic diseases such as acute pancreatitis, chronic pancreatitis, characterized by an increase in the plasma lipase level in humans or animals, compared to the plasma lipase level in a healthy individual, or renal failure, abdominal trauma (ischemia, mesenteric infarct, intestinal perforation or occlusion).

The invention also relates to a method for the preparation of microtitration plates comprising wells coated with a lipid substrate which is able to be hydrolyzed by a lipase or phospholipase by releasing α-eleostearic acid, characterized in that it comprises the following stages:

the addition to the wells of said plates of a composition comprising the lipid substrate in solution in an appropriate solvent capable of being evaporated off under vacuum, such as hexane or petroleum ether, this addition being if appropriate carried out after washing the wells of said plates with said solvent, evaporation under vacuum of said solvent until the formation of a coating of said lipid substrate of approximately 0.5 to approximately 5 μm, and preferably approximately 1 μm in thickness on the walls of the wells of the microtitration plates.

A subject of the invention is also the microtitration plates comprising wells coated with a lipid substrate which is able to be hydrolyzed by a lipase or phospholipase by releasing α-eleostearic acid, as obtained by the above-mentioned method, the coating of said lipid substrate on the walls of the wells of the microtitration plates being approximately 0.5 to approximately 5 μm, and preferably approximately 1 μm in thickness.

A more particular subject of the invention is the use of the above-mentioned microtitration plates comprising wells coated with a lipid substrate, for the implementation of a method for the detection and/or measurement in vitro of a lipase or phospholipase activity as defined above, or for the implementation of a method for screening inhibitors of lipolytic enzymes (inhibitors of lipases or phospholipases) comprising a stage of measuring their possible ability to inhibit said enzymes thanks to the method for the detection and/or measurement in vitro of a lipase or phospholipase activity according to the invention.

FIGURE LEGENDS

Figure 2A:
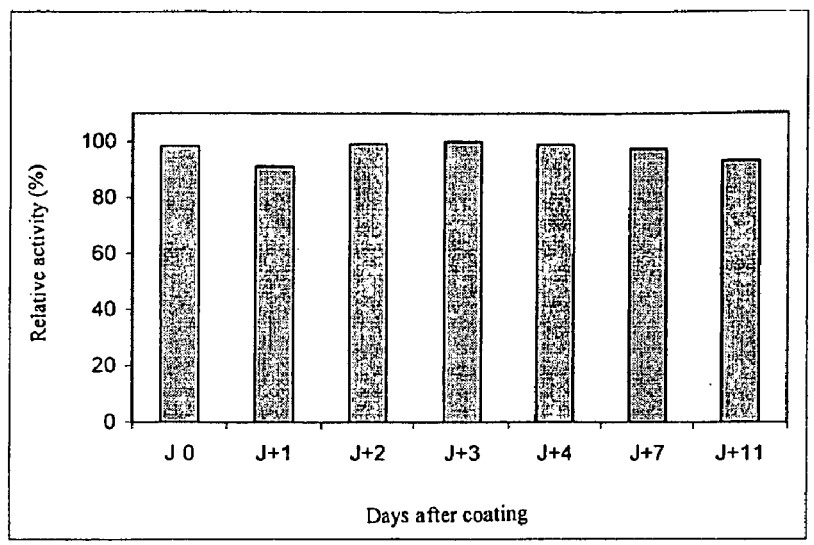
FIGS. 2a and 2b represent the stability of the adsorbed or emulsified lipid substrate.

In FIG. 2a, the microplate has been prepared by "coating" with S citronellol-α-eleostearate ester (80 μg/well) and stored for several days at 4° C. The stability of the coating was studied by assay of the lipolytic activity of the $Thermomyces$ $lanuginosus$ lipase (TLL) (10 nM final) on different days after the "coating" with the ester in a buffer Tris 10 mM pH 8.0, $CaCl_2$ 6 mM, EDTA 1 mM, BHT 0.001% and β-cyclodextrin 3 mg/mL. FIG. 2a represents the relative enzymatic activity (%) for several days after the "coating".

Figure 2B:
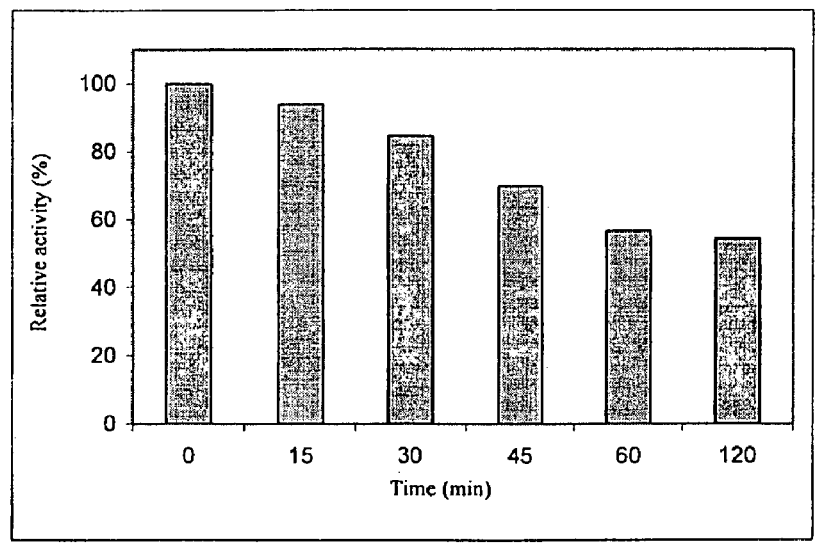

In FIG. 2b, emulsions with 20 μg/mL of S citronellol α-eleostearate were produced and distributed (200 μL) into each well of the microtitration plate. The stability of the emulsions is tested by measuring the activity of the TLL at different times after the emulsification, as described above for FIG. 2a.

Figure 3:
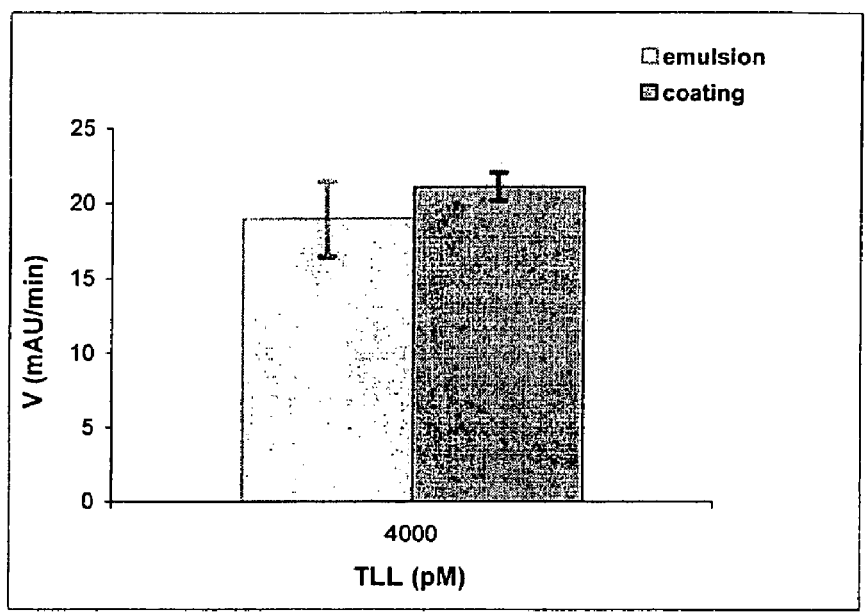

FIG. 3 represents the reproducibility of the activities of the TLL assayed on the S citronellol-α-eleostearate ester either "coated" or in emulsion. The activity of the TLL (4 nM) was tested on the S citronellol-α-eleostearate ester either adsorbed (80 μg/well) or in emulsion (20 μg/mL) in a microplate in a buffer Tris 10 mM pH 8.0, $CaCl_2$ 6 mM, EDTA 1 mM, BHT 0.001% and β-cyclodextrin 3 mg/mL. The speeds are expressed in milli-units of absorbance appearing per minute (mAU/min). The variability of the results was calculated over 8 experiments for each of the experimental conditions.

FIGS. 4A and 4B represent the inhibition kinetics of HPL (human pancreatic lipase) by THL (tetrahydrolipstatin). The microplate is prepared by "coating" with triglycerides (50 μg/well) extracted from tung oil which contains a high proportion of a-eleostearic acid. A solution (200 μl) of Tris buffer is added to the wells. The activity of the HPL alone, or pre-incubated with the THL, is measured by recording the optical density (method A; FIG. 4A). FIG. 4A represents the optical density (OD) at 272 nm as a function of time. The curve with the black circles corresponds to the lipase HPL alone; the curve with the black squares corresponds to the lipase HPL pre-incubated with THL in a ratio of 1:100 and the curve with the white circles corresponds to the lipase HPL pre-incubated with THL in a ratio of 1:50.

FIG. 4B corresponds to a different protocol (method B): after the injection of HPL (at a final concentration of 2 nM), THL is injected into the reaction medium (at a final concentration of 10 nM) during lipolysis.

The invention is further illustrated by the detailed description which follows of the implementation of a method for the measurement of a lipase activity using the microtitration plates according to the invention (so-called "coating" method), compared with a so-called "emulsion" method for measurement.

Figure 1:
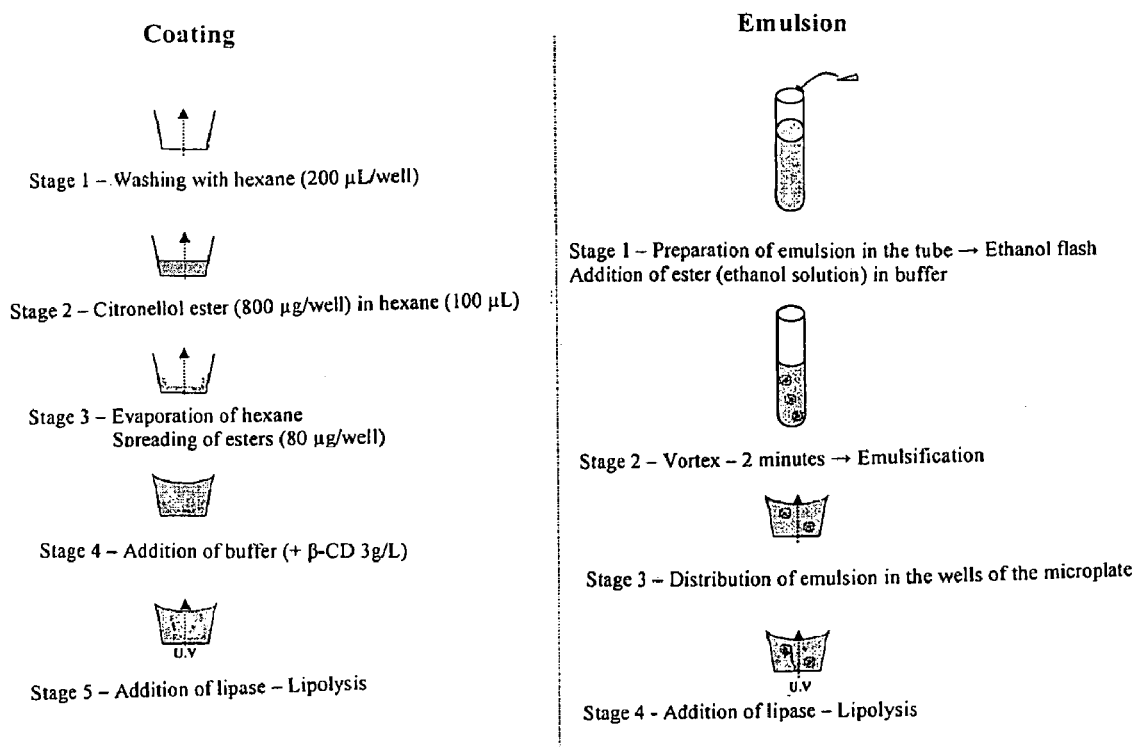
FIG. 1 represents the preparation protocols for the microplates: "Coating"versus emulsion. The lipid substrate is adsorbed in each well of the microplate ("Coating") or prepared in emulsion then deposited in the microplate (Emulsion).

This study has been carried out by running in parallel the study of the lipase activity either by "coating" with lipids (natural triglycerides or synthetic esters) or on emulsions produced beforehand in a tube, before distribution of the samples into the microplate wells (FIG. 1).

The study compared "coating" versus "emulsion" using enantiomeric esters (R or S citronellola-eleostearate) and clearly shows that the "coating" of these substrates onto the microplate has several advantages:

1. Better Storage of the Coated Substrates Over Time

A solution of citronellol α-eleostearate was "coated" (80 μg/well) onto the 96 wells of a microplate. The activity of $Thermomyces$ $lanuginosus$ lipase (TLL) (10 nM, final concentration) was then tested on different days after the "coating". The microplate was stored at 4° C., with or without buffer in the wells. On the graph of FIG. 2a, it can be seen that the activity of the lipase remains constant over time, indicating that the binding of the substrate to the microplate is reproducible and stable at least for 20 days.

In parallel, the emulsions at 20 μg/mL of S citronellol α-eleostearate are produced by injecting 12 μL of an ester solution (5 mg/mL in ethanol-BHT (Butylated HydroxyToluene) 0.001%) into lipase activity buffer (qs 3 mL), thus creating an ethanol flash. The solution is then stirred with a "vortex" for 2 minutes. The stability of the emulsions is tested by measuring the activity of TLL (10 nM) at different times after the emulsification. The lipase activity is not constant over time and it reduces significantly 30 minutes after the production of the emulsion (FIG. 2b). These results indicate that the emulsions cannot be stored and therefore must be used immediately after their production. This is a major drawback compared with the <<coating>> of the microplate substrates which can be produced several days in advance.

2. Activity of the Lipases Higher on the "Coated" Substrate than on the Emulsion The activity of the lipase is higher with the "coated" substrate than with the emulsion substrate (see FIG. 3).

3. Better Reproducibility of the Experiments with the "Coated" Substrate

The dispersion of the results obtained by calculating the averages and the standard deviations over 8 experiments is more significant with the emulsion substrates (FIG. 3). In addition, it is difficult to produce the emulsions in a reproducible fashion (cf. above).

In conclusion, the development of this microplate test is a method representing an innovative character compared with all the previous methods (Beisson et al., Eur. J. Lipid Sci. Technol. 2000, 2: 133-153) for the rapid and continuous assay of lipases with natural triglycerides, residing in the spectral properties in the UV of α-eleostearic acid. This is a sensitive and reproducible test. The "coating" of the substrate makes it possible to prepare a microplate in advance and to store it for at least two weeks in a cold room, without specific precautions. On the other hand the emulsification technique, as published by Pencreac'h et al. (Anal Biochem. 2002; 303: 17-24), has numerous drawbacks, namely instability of the emulsions, lower lipolytic activity etc.

Compared to the previous publication (Pencreac'h et al., Anal Biochem. 2002; 303: 17-24), the present invention proposes two important technical improvements:

High flow rate: Adaptation of the principle of the published method (Pencreac'h et al., Anal Biochem. 2002; 303: 17-24) to a high flow rate system (96-well microplate).

"Coating" of lipid substrates in the wells of the microtitration plates with a considerably longer storage period.

Use of the Plates of the Invention for the Implementation of a Method for the Screening Inhibitors of Lipolytic Enzymes The microtitration plates comprising wells coated with a lipid substrate which is able to be hydrolyzed by a lipase or a phospholipase A1 or A2 by releasing α-eleostearic acid, obtained according to the method of the invention, are used for the screening at high flow rates of inhibitors and for measurement of the inhibition of lipases or phospholipases A1 or A2.

Example of Tetrahydrolipstatin (Orlistat or THL): Powerful Inhibitor of the Digestive Lipases
(see the following articles: Digestive lipases inhibition: an in vitro study. Tiss A., Miled N., Verger R., Gargouri Y., Abousalham A., 2004, Lipases and phospholipases in drug development from biochemistry to molecular pharmacology, Wiley VCH (Muller G. and Petry S., Eds), 155, 193; Covalent inactivation of lipases. Ransac S., Gargouri Y., Marguet F., Buono G., Beglinger C., Hildebrand P., Lengsfeld H., Hadvary P., Verger R., 1997, Methods in Enzymol., 286, 190-231).

The microtitration plates, with "coating" of the lipid substrate, are prepared as has been described above. A solution constituted by Tris buffer and β-cyclodextrin (3 mg/ml) is added into the wells. The optical density at 270 nm is recorded as a function of time for 5 to 10 min (see FIGS. 4A and 4B). A solution of human pancreatic lipase (HPL), alone or pre-incubated with THL (inhibitor), is injected into the wells. The enzymatic activity is then recorded as a function of time by measurement of the OD at 272 nm (method A; FIG. 4A). The pre-incubation of HPL with THL, at a molar excess of 1 to 100 or of 1 to 50 for 10 min, reduces the initial lipase activity by 75% or 40% respectively (see FIG. 4A).

The effect of THL on the lipase activity has also been measured by injecting THL during lipolysis (method B; FIG. 4B). The injection of THL (at a final concentration of 10 nM) reduces the activity of HPL by approximately 40%.

CONCLUSION

In view of the results presented in FIGS. 4A and 4B, it should be noted that the present invention is perfectly suited to the measurement at high flow rates of the inhibition of lipases, and therefore to the screening of inhibitors of lipases and phospholipases A1 and A2.

The invention claimed is:

1. A method for preparing microtitration plates comprising wells coated with a lipid substrate onto which α-eleostearate groups are bound covalently, said method comprising the steps of:

adding to the wells of said plates said lipid substrate onto which α-eleostearate groups are bound covalently, said lipid substrate being in solution in a solvent; and evaporating under vacuum said solvent until a coating of said lipid substrate having a thickness of approximately 0.5 to approximately 5 μm is formed on the walls of the wells of the microtitration plates, wherein said lipid substrate is selected from the group consisting of:

(i) purified triglycerides of tung oil of general formula

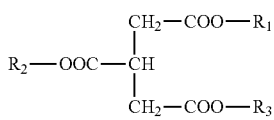

where $R_1$ and $R_3$ represent identical or different fatty acid residues comprising 12 to 20 carbon atoms, and said fatty acid residues optionally having one or more unsaturations, and where $R_2$ represents α-eleostearic acid, (ii) lipids containing 1 or 2 α-eleostearate chains in a position that provides regioselectivity of a lipase or a phospholipase, said lipids selected from the group consisting of diglycerides, monoglycerides, cholesterol esters and phospholipids, (iii) citronellol α-eleostearate of the following formula:

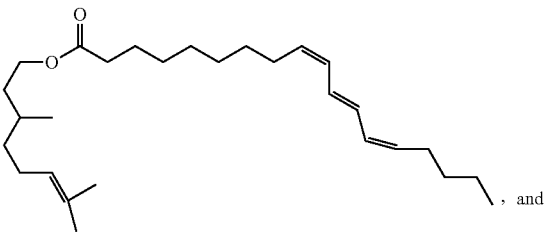

, and (iv) acid esters of α-eleostearate with molecules selected from the group consisting of propanolol, sotalol, carvedilol, and menthol.

2. Microtitration plates comprising wells coated with a lipid substrate onto which α-eleostearate groups are bound covalently, said lipid substrate is selected from the group consisting of:

(i) purified triglycerides of tung oil of general formula

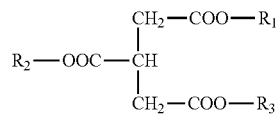

where $R_1$ and $R_3$ represent identical or different fatty acid residues comprising 12 to 20 carbon atoms, and said fatty acid residues optionally having one or more unsaturations, and where $R_2$ represents α-eleostearic acid, (ii) lipids containing 1 or 2 α-eleostearate chains in a position that provides regioselectivity of a lipase or a phospholipase, said lipids selected from the group consisting of diglycerides, monoglycerides, cholesterol esters and phospholipids, (iii) a citronellol α-eleostearate of the following formula:

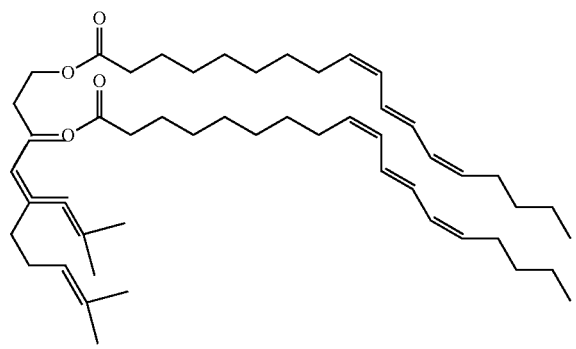

and (iv) acid esters of α-eleostearate with molecules selected from the group consisting of propanolol, sotalol, carvedilol, and menthol, said microtitration plates being obtained by a method comprising the steps of:

adding to the wells of said plates of said lipid substrate onto which α-eleostearate groups are bound covalently, said lipid substrate being in solution in a solvent; and evaporating under vacuum said solvent until a coating of said lipid substrate having a thickness of approximately 0.5 to approximately 5 μm is formed on the walls of the wells of the microtitration plates.

* * * * *